United States Patent [19]

Kawajiri et al.

[11] Patent Number: 4,873,217

[45] Date of Patent: Oct. 10, 1989

[54] CATALYST FOR OXIDATION OF OLEFIN OR TERTIARY ALCOHOL AND PROCESS FOR PRODUCTION THEREOF

[75] Inventors: Tatsuya Kawajiri; Hideo Onodera; Shinichi Uchida, all of Himeji; Yukio Aoki, Taishi; Masahiro Wada, Nishinomiya, all of Japan

[73] Assignee: Nippon Shokubai Kagaku Kogyo Co., Ltd., Osaka, Japan

[21] Appl. No.: 156,669

[22] Filed: Feb. 17, 1988

[30] Foreign Application Priority Data

Feb. 17, 1987 [JP] Japan ................................. 62-32354
Jun. 18, 1987 [JP] Japan ................................ 62-150112

[51] Int. Cl.$^4$ .......................... B01J 23/78; B01J 23/84; B01J 23/88
[52] U.S. Cl. .................... 502/311; 502/205; 502/212; 502/215; 502/242; 502/243; 502/249; 502/304
[58] Field of Search ............... 502/311, 205, 212, 215, 502/242, 243, 249, 304

[56] References Cited

U.S. PATENT DOCUMENTS

| | | | |
|---|---|---|---|
| 4,001,317 | 1/1977 | Grasselli et al. | 502/311 X |
| 4,049,577 | 9/1977 | Childress et al. | 502/311 X |
| 4,166,808 | 9/1979 | Daumas et al. | 502/311 X |
| 4,259,211 | 3/1981 | Krabetz et al. | 252/443 |
| 4,276,196 | 6/1981 | Dalton et al. | 252/435 |
| 4,332,971 | 6/1982 | Dalton et al. | 568/480 |
| 4,442,308 | 4/1984 | Arntz et al. | 568/480 |
| 4,511,671 | 4/1985 | Saito et al. | 502/311 X |
| 4,548,709 | 10/1985 | Bowes et al. | 208/213 |
| 4,556,731 | 12/1985 | Guttmann et al. | 562/546 |

OTHER PUBLICATIONS

Chemical Abstracts, vol. 88, No. 12, 79851b, Takeda Chemical Industries Ltd.

*Primary Examiner*—W. J. Shine
*Attorney, Agent, or Firm*—Sherman and Shalloway

[57] ABSTRACT

A catalyst used for producing, by catalytic gas phase oxidation of a $C_3$–$C_5$ oelfin or tertiary alcohol, the corresponding unsaturated aldehyde and unsaturated carboxylic acid, said catalyst characterized by comprising molybdenum, iron and bismuth and having a specific surface area in the range from 1 to 20 m$^2$/gr, a pore volume in the range from 0.1 to 1.0 cc/gr and a pore diameter distribution in which the pore diameters are collectively distributed in the range of each of from 1 to 10 microns and from 0.1 to less than 1 micron; and a process for preparing said catalyst by charging an unfired material power into a centrifugal flow coating device to form particles having the average particle diameter of 2 to 10 mm and then firing the particles.

15 Claims, No Drawings

CATALYST FOR OXIDATION OF OLEFIN OR TERTIARY ALCOHOL AND PROCESS FOR PRODUCTION THEREOF

This invention relates to an oxide catalyst comprising molybdenum, iron and bismuth and being suitable for producing, from an olefin or tertiary alcohol, the corresponding unsaturated aldehyde and unsaturated carboxylic acid and a process for the production thereof. More specifically, this invention relates to a catalyst which exhibits high activity and excellent durability owing to its specific properties and which is used for the oxidation of an olefin or tertiary alcohol and a process for the production of said catalyst with good reproducibility.

There are proposals for various catalysts for producing, from an olefin or tertiary alcohol (especially tertiary butanol), the corresponding unsaturated aldehyde (and unsaturated carboxylic acid) at high yields by a catalytic gas phase oxidation reaction. These proposals are mainly concerned with selection of components for catalysts and ratios thereof, and some of them are also concerned with selection of catalyst properties and production processes with reproducibility. For example, there are many proposals concerning catalyst properties such as specific surface area, pore volume, pore diameter, etc., with regard to catalysts used for the oxidation and ammoxydation reactions of an olefin and comprising molybdenum, bismuth and iron. However, none of these proposed catalysts are on a satisfactory level, as will be mentioned hereinbelow.

With regard to the specific surface area, catalysts having specific surface areas in the range from 0.01 to 50 $m^2/g$ are described in Japanese Patent Publications Nos. 21081/1972, 10434/1977, 13488/1969, 5632/1978, 36384/1980, 24658/1981, 28180/1981 and 29139/1983 and Japanese Laid-Open Patent Publication No. 26690/1973. However, these catalysts are not satisfactory as industrial catalysts, since they have low activity in spite of defined high reaction temperatures or they have low selectivity to a corresponding unsaturated aldehyde. With regard to the pore volume, Japanese Laid-Open Patent Publication No. 119837/1982 describes that the pore volume of 0.2 to 0.4 cc/g is preferable. However, Examples thereof merely disclose the use mainly in ammoxydation. With regard to the pore diameter, the same Japanese Laid-Open Patent Publication No. 119837/1982 describes that the average pore radius of not less than 2,000 Å is preferable. The pore radii therein are controlled by addition of organic substance such as cellulose, etc., to material for catalyst. Japanese Patent Publication No. 113141/1983 describes, with regard to the pore diameter, that the pores having a diameter smaller than 100 Å should be less than 3%. However, the catalysts disclosed therein all have low activity, and none of them can be used as an industrial catalyst for producing acrolein and acrylic acid or methacrolein and methacrylic acid at high yields by oxidation of propylene, isobutylene or tertiary butanol.

In the case of producing acrolein and acrylic acid or methacrolein and methacrylic acid by an oxidation reaction of propylene, isobutylene or tertiary butanol by the use of a reaction apparatus having a fixed bed or moving bed, catalysts are used, in general, in the form of pellets having a suitable size. Such pellets are formed by using a tablet-forming machine, extruder, pill-forming machine, rolling particle-forming machine, etc. However, there are many cases where it is difficult to form pellets without degradation of catalyst performance, and most cases show poor reproducibility of catalyst performance.

Therefore, the present inventors made an assiduous study of those causes of variations of catalyst performance which take place at the time of preparing catalyst pellets. As a result, they have found that, in catalysts containing Mo, Fe and Bi as essential components, the catalyst performance decreases to a great extent and the performance and physical property values vary depending upon the methods of formation thereof. The main cause thereof is that the forming procedure has influence on the pores of a catalyst and has consequent influence on the specific surface area, pore volume and average pore diameter of the catalyst.

As a result of the present inventor's further study, they have found that a catalyst containing Mo, Fe and Bi as essential components has to meet three conditions, in order to exhibit excellent properties, that it has a specific surface area in the range from 1 to 20 $m^2/gr$, preferably from 5 to 20 $m^2/gr$, that it has a pore volume in the range from 0.1 to 1.0 cc/gr, preferably from 0.3 to 0.9 cc/gr, and that it has a pore diameter distribution in which its pore diameters are collectively distributed in the range of each of from 1 to 10 $\mu m$ and from 0.1 to less than 1 $\mu m$.

Accordingly, the present invention provides a catalyst which comprises containing Mo, Fe and Bi and having the above three properties in combination and which is used for producing, by catalytic gas phase oxidation of a $C_3$–$C_5$ olefin or tertiary alcohol, the corresponding unsaturated aldehyde and unsaturated carboxylic acid.

In the present invention, the well-balanced presence of pores having pore diameters of 1 to 10 $\mu m$ and pores having pore diameters of 0.1 to less than 1 $\mu m$ is one of the important conditions. Catalysts for an oxidation reaction of propylene exhibit performance enhanced in both catalyst activity and selectivity when the catalysts have a pore diameter distribution in which the pore volume consisting of pores having pore diameters in the range from 0.1 to less than 1 $\mu m$ is not less than 30%, preferably in the range from 45 to 80%, based on the entire pore volume and the pore volume consisting of pores having pore diameters in the range from 1 to 10 $\mu m$ is not less than 20%, preferably in the range from 25 to 60%, based on the entire pore volume. On the other hand, it is one of the important conditions for the performance of catalysts used for an oxidation reaction of isobutylene or tertiary butanol that the ratio of the pore volume consisting of pores having pore diameters in the range from 1 to 10 $\mu m$ should be greater than the ratio of the pore volume consisting of pores having pore diameters in the range from 0.1 to less than 1 $\mu m$.

In general, a pore having a smaller pore diameter has a larger contribution toward the surface area and pore volume. However, in the catalyst comprising Mo, Fe and Bi for oxidation of an olefin or tertiary alcohol in the present invention, the mere larger ratio of the smaller pores [i.e., pores having pore diameters in the range of 0.1 to less than 1 $\mu m$] is not sufficient to obtain the aforementioned activity and selectivity, and the fairly larger ratio of the larger pores (i.e., pores having pore diameters in the range of 1 to 10 $\mu m$) is necessary as well.

By forming an unfired catalyst material powder into pellets having the average diameter of 2 to 10 mm by the use of a centrifugal flow coating device, the catalyst having the above physical properties in the present invention can be obtained with very good reproducibility as compared with usual formation methods. In usual formation methods of catalysts, a rolling particle-forming method, marmerizer forming method, fluidized bed particle-forming method, etc., are used for the preparation of spherical shapes, and an extrusion method, tablet-forming method, etc., are used for cylindrical shapes. However, in the case of using these formation methods, it is difficult in many cases to form catalysts without degrading the catalyst performance, the performance varies widely and the reproducibility is often poor. In contrast thereto, in the present invention, the use of a centrifugal flow coating device, which is simple and good in producibility, makes it possible to prepare spherical or particulate catalysts having the aforespecified specific surface area, pore volume and pore diameter distribution, with good reproducibility. Further, the formation by a centrifugal flow coating device has advantages that catalysts having a narrow distribution of particle size can be obtained and that, since said catalysts are particulate or spherical, the catalysts have high mechanical strength, little pressure loss and high resistance to wear and are easy to fill in or take out from a reaction apparatus.

A centrifugal flow coating device and the use thereof are known as one method of forming powder material into particles. For example, Japanese Patent Publication No. 10878/1971 discloses them as a method of forming sugar coatings of medicaments, and Japanese Patent Publication No. 17292/1977 discloses the coating of particulate cores with a catalyst or carrier by a centrifugal flow coating device.

The present invention applies this method to the preparation of an oxide catalyst comprising Mo, Fe and Bi elements as essential components, and easily makes it possible to obtain a spherical or particulate catalyst having the aforespecified specific surface area, pore volume and pore diameter distribution and having high physical strength, by only using, as a binder, a liquid such as water, or by optionally using, in combination therewith, a substance which gives pores into a catalyst by combustion or volatility at the time of firing.

As a preparation example by a centrifugal flow coating device, there can be cited a method which comprises charging a powder of an unfired oxide composition not shaped or pre-stage catalyst particle material composition not converted to oxide into a centrifugal flow coating device, forming the powder into particles with blowing heated air thereinto and spraying a binder such as water, taking out the particles grown to the desired size in batch-type operation or in successive operation, then drying the particles as necessary and thereafter firing them.

The catalyst of the present invention can be used by diluting it with an inert carrier or by holding it on an inert carrier according to a case where it is necessary. In the formation of particles, it is preferable to use, as a core, granules obtained by preforming a powder of catalyst per se to a size about 10 times as large as that of the material powder. Naturally, an inert carrier can be also used as this core. Examples of the inert carrier include silicon carbide, silica, alpha-alumina and others known as a refractory material. With regard to a catalyst powder for coating to grow a particle diameter, it is preferable to preadjust it to not more than 100 mesh.

In order to produce a catalyst having the specific surface area, pore volume and pore diameter distribution specified by the present invention with good reproducibility, it is possible to add, for example, a polyvinyl alcohol, stearic acid, etc., to a material particles at the time of preparation of a catalyst powder or add it to a catalyst powder at the time of shaping. In the case, for example, when it is necessary to make the degree of powdering smaller, it is possible to use a whisker or glass fiber. As a binder of the powder, it is also possible to use water, cellulose, ammonium nitrate, graphite, starch, etc. Organic solvents such as alcohol, acetone, etc., can be used as well.

The catalyst of the present invention comprises Mo, Fe and Bi as essential components. Most preferably, it has a composition represented by the following formula,

$$Mo_aW_bBi_cFe_dA_eB_fC_gD_hO_x$$

wherein Mo denotes molybdenum, W denotes tungsten, Bi denotes bismuth, Fe denotes iron, A denotes at least one element selected from the group consisting of nickel and cobalt, B denotes at least one element selected from the group consisting of alkali metal, alkaline earth metal and thallium, C denotes at least one element selected from the group consisting of phosphorus, tellurium, antimony, tin, cerium, lead, niobium, boron, arsenic, manganese and zinc, D denotes at least one element selected from the group consisting of silicon, aluminum, titanium and zirconium, and O denotes oxygen; and further, a, b, c, d, e, f, g, h and x denote atomic ratios respectively, when the olefin is propylene and when $a=2$ to 12, $b=0$ to 10 and $a+b=12$, then $c=0.1$ to 10, $d=0.1$ to 10.0, $e=2$ to 20, $f=0.005$ to 3.0, $g=0$ to 4.0, $h=0.5$ to 15 and x is a numerical value determined depending upon the atomic values of the other elements than oxygen, and when the olefin is isobutylene or when the tertiary alcohol is tertiary butanol and when $a=12$, then $b=0$ to 10, $c=0.1$ to 10, $d=0.1$ to 20, $e=2$ to 20, $f=0$ to 10, $g=0$ to 4, $h=0$ to 30 and x is a numerical value determined depending upon the atomic values of the other elements than oxygen.

A catalytic gas phase oxidation using a catalyst of the present invention is carried out by introducing a mixture gas consisting of 1.0 to 10% by volume of an olefin or tertiary butanol, 3 to 20% by volume of molecular oxygen, 0 to 60% by volume of water vapor and 20 to 80% by volume of an inert gas such as nitrogen, carbon dioxide gas, etc., onto the catalyst at a temperature in the range from 250° to 450° C., at a pressure of an atmospheric pressure to 10 atm and at a space velocity of 300 to 7,000 hr$^{-1}$ (STP).

The following Examples and Comparative Examples will illustrate the present invention more in detail, however, the present invention is not limited thereto. In the present specification, the conversion, selectivity and total yield in a single flow are respectively defined as follows.

Conversion ratio (mol %) =

$$\frac{\text{Number of moles of reacted propylene, isobutylene or tertiary butanol}}{\text{Number of moles of charged propylene, isobutylene or tertiary butanol}} \times 100$$

Selectivity (mol %) =

-continued $$\frac{\text{Number of moles of produced acrolein and acrylic acid or methacrolein and methacrylic acid}}{\text{Number of moles of reacted propylene, isobutylene or tertiary butanol}} \times 100$$

Total yield of a single flow (mol %) =

$$\frac{\text{Number of moles of produced acrolein and acrylic acid or methacrolein and methacrylic acid}}{\text{Number of moles of charged propylene, isobutylene or tertiary butanol}} \times 100$$

[EXAMPLE I]

Preparation of suspension of catalyst material

While 4,500 ml of distilled water was heated with stirring, 3,186 g of ammonium molybdate and 972 g of ammonium paratungstate were added and dissolved therein. Separately, a solution of 2,100 g of cobalt nitrate in 400 ml of distilled water, a solution of 729 g of ferric nitrate in 600 ml of distilled water and a solution of 876 g of bismuth nitrate in 900 ml of distilled water acidified by addition of 180 ml of conentrated nitric acid were prepared respectively, and a mixture of these three nitrate solutions was added to the above water solution containing ammonium molybdate and ammonium paratungstate. Then, a liquid obtained by dissolving 732 g of silica sol containing 20% by weight of silica and 6.06 g of potassium hydroxide in 450 ml of distilled water was added and stirred to prepare the suspension. (This suspension is referred to as suspension-A.)

EXAMPLE I-1

(Centrifugal flow coating method)

The suspension-A was heated, stirred, evaporated and dried to solidify it, and then the resulting solid was milled to about 100 mesh to obtain a powder. This powder was charged into a centrifugal flow coating device blowing heated air at 90° C. with using distilled water as a binder, and formed into spherical particles having the average diameter of 5 mm. These particles were dried in a drier at 120° C. for 12 hours and then fired under an air current at 450° C. for 6 hours to prepare a catalyst (I-1). The ratio of elements other than oxygen in this catalyst oxide was $Co_4Bi_1Fe_1W_2Mo_{10}Si_{1.35}K_{0.06}$.

EXAMPLES I-2-1 AND I-2-2

(Tablet forming method)

A suspension-A was prepared in the same way as in the above, and the suspension-A was evaporated with stirring under heat to solidify it. Then the resulting solid in block state was dried in a drier under air current at 200° C. for 12 hours. The dried block was milled to not more than 100 mesh. 2% by weight of a carbon powder was added to this milled powder and the resulting mixture was formed into tablets having a diameter of 5 mm and height of 5 mm. The tablets were fired under air current at 450° C. for 6 hours to prepare a catalyst (I-2-1). Then, the same procedure was repeated to prepare a catalyst (I-2-2).

EXAMPLES I-3-1 AND I-3-2

(Extrusion method)

A suspension-A was prepared in the same way as in the above, and the suspension-A was condensed until it was extrudable, and extruded to form extrudates having a diameter of 5 mm and height of 5 mm. The extrudates were dried at 120° C. for 12 hours and fired under air current at 450° C. for 6 hours to prepare a catalyst (I-3-1). Then, the same procedure was repeated to prepare a catalyst (I-3-2).

EXAMPLE I-4

(Marmerizer-forming method)

A suspension-A was prepared in the same way as in the above, and the suspension-A was treated with externally applied heat for condensation thereof to obtain a soil-like product, 40% by weight of which was dissipated when it was fired at 500° C. (i.e., its solid content was 60% by weight). This product was extruded to form extrudates having a diameter of 6 mm and lengths of 4 to 7 mm, and then the extrudates were subjected to a marmerizer to form elliptic spheres having a breadth of 3 mm and length of 5 mm. The elliptic spheres were dried at 120° C. for 12 hours and fired under air current at 450° C. for 6 hours to prepare a catalyst (I-4-1).

EXAMPLE I-5

(Rolling particle-forming method)

A suspension-A was prepared in the same way as in the above, and the suspension-A was evaporated and dried with stirring under heat to solidify it. The resulting solid was milled to about 100 mesh to obtain a powder. This powder was formed into spherical particles having the average diameter of use of a rolling particle-forming machine and heated air at 80° C. and distilled water as a binder. The particles were dried at 120° C. for 12 hours and then fired under air current at 450° C. for 6 hours to prepare a catalyst (I-5).

EXAMPLE I-6

(Pill-forming method)

A suspension-A was prepared in the same way as in the above, and the suspension-A was treated with externally applied heat for condensation thereof to obtain a soil-like product, 45% by weight of which was dissipated when it was fired at 500° C. (i.e., its solid content was 55% by weight). This product was formed into shapes having the average diamter of 5 mm by the use of a usual pill-forming machine. This resulting spherical product was dried at 120° C. for 12 hours and then fired under air current at 450° C. for 6 hours to obtain a catalyst (I-6).

REACTION TEST

Catalysts I-1 to I-6 obtained in the above EXAMPLES (1,500 ml each) were charged respectively to steel reaction tubes having an internal diameter of 25.4 mm, and a mixture gas composed of 7% by volume of propylene, 12.6% by volume of oxygen, 10% by volume of water vapor and 70.4% by volume of nitrogen was introduced thereinto to carry out catalytic gas phase oxidation reactions of propylene at a reaction temperature of 310° C. for a contact time of 2.25 seconds. The results are shown in Table 1.

[EXAMPLE II]

(Preparation of catalyst and its reproducibility)

Catalyst material suspensions-A were prepared on a scale four times as large as that of EXAMPLES I-1 to I-6 series, and catalysts (EXAMPLES II-1 to II-4) were prepared by using the suspensions-A, by using forming methods shown in Table 2 and according to EXAMPLE I. In each of EXAMPLES II-1 to II-4, four catalysts were prepared under the same conditions (batch Nos. 1 to 4) in order to test the presence or absence of the reproducibility of catalyst preparation. Tests of performance were carried out according to the method of EXAMPLES I-1 to I-6. The results are shown in Table 2.

As is clear in Table 2, it is seen that the formation of a centrifugal flow coating method can give catalysts having smaller variation of physical values and high activity. The fact that the variation of physical values is small means that catalysts were prepared with good reproducibility. On the other hand, it is further seen that catalysts prepared by the other forming methods include those that have not the specific surface area, pore volume and pore diameter specified by the present invention although they were prepared in batches under entirely the same conditions, and that the catalyst performance thereof is inferior to that of the catalysts obtained by a centrifugal flow coating method.

[EXAMPLE III]

Preparation of catalyst material suspension

The preparation of the catalyst material suspension for EXAMPLES I-1 to I-6 series was repeated except that thallium nitrate and barium nitrate were used in place of potassium hydroxide. The resulting suspension is referred to as suspension-B.

EXAMPLE III-1

(Centrifugal flow coating method)

The suspension-B was treated in the same way as in EXAMPLE I-1 to prepare a catalyst. The ratio of elements other than oxygen in this catalyst oxide was $Co_4Bi_1Fe_1W_2Mo_{10}Si_{1.35}Tl_{0.04}Ba_{0.05}$.

EXAMPLES III-2-1 AND II-2-2

(Tablet-forming method)

The suspension-B was treated according to the process described in EXAMPLE I-2 to prepare catalysts.

[EXAMPLE IV]

Preparation of catalyst material suspension

The preparation of the catalyst material suspension for EXAMPLES I-1 to I-6 series was repeated except that cesium nitrate was used in place of potassium hydroxide, and further, titanium dioxide was also used together with silica sol containing 20% by weight of silica. The resulting suspension is referred to as suspension-C.

EXAMPLE IV-1

The suspension-C was treated in the same way as in EXAMPLE I-1 to prepare a catalyst. The ratio of elements other than oxygen in this catalyst oxide was $Co_4Bi_1Fe_1W_2Mo_{10}Si_{1.35}Cs_{0.02}Ti_{1.0}$.

EXAMPLES IV-2-1 AND IV-2-2

(Extrusion method)

The suspension-C was treated according to EXAMPLE I-3 to prepare catalysts.

[EXAMPLE V]

Preparation of catalyst material suspension

The preparation of the catalyst material suspension for EXAMPLES I-1 to I-6 series was repeated except that strontium nitrate was used in place of potassium hydroxide. The resulting suspension is referred to as suspension-D.

EXAMPLE V-1

(Centrifugal flow coating method)

The suspension-D was treated in the same way as in EXAMPLE I-1 to prepare a catalyst. The ratio of elements other than oxygen in this catalyst oxide was $Co_4Bi_1Fe_1W_2Mo_{10}Si_{1.35}Sr_{0.06}$.

EXAMPLES V-2-1 AND V-2-2

(Marmerizer-forming method)

The suspension-D was treated according to EXAMPLE I-4 to prepare catalysts.

[EXAMPLE VI]

Preparation of catalyst material suspension

The preparation of the catalyst material suspension for EXAMPLES I-1 to I-6 series was repeated except that calcium nitrate was used in place of potassium hydroxide, and further, silica sol and calcium nitrate were added and then niobium pentoxide was added. The resulting suspension is referred to as suspension-E.

EXAMPLE VI-1

(Centrifugal flow coating method)

The suspension-E was treated in the same way as in EXAMPLE I-1 to prepare a catalyst. The ratio of elements other than oxygen in this catalyst oxide was $Co_4Bi_1Fe_1W_2Mo_{10}Si_{1.35}Ca_{0.06}Nb_{0.5}$.

EXAMPLES VI-2-1 AND VI-2-2

(Rolling particle-forming method)

The suspension-E was treated according to EXAMPLE I-5 to prepare catalysts.

[EXAMPLE VII]

Preparation of catalyst material suspension

In preparing a catalyst material suspension in the same way as in the preparation of the catalyst suspension for EXAMPLES I-1 to I-6 series, nickel nitrate was added together with cobalt nitrate, rubidium nitrate was used in place of potassium hydroxide and phosphoric acid was used in place of ammonium paratungstate. The resulting suspension is referred to as suspension-F.

EXAMPLE VII-1

(Centrifugal flow coating method)

The suspension-F was treated in the same way as in EXAMPLE I-1 to prepare a catalyst. The ratio of elements other than oxygen in this catalyst oxide was $Co_3Ni_1Bi_1Fe_2Mo_{12}Si_{4.7}P_{1.0}Rb_{0.1}$.

EXAMPLES VII-2-1 and VII-2-2

(Pill-forming method)

The suspension-F was treated according to EXAMPLE I-6 to prepare catalysts.

[EXAMPLE VIII]

Preparation of catalyst material suspension

In preparing a catalyst material suspension in the same way as in the preparatiin of the catalyst suspension for EXAMPLES I-1 to I-6 series, nickel nitrate and aluminum nitrate were added together with cobalt nitrate and boric acid was used in place of ammonium paratungstate. The resulting suspension is referred to as suspension-G.

EXAMPLE VIII-1

(Centrifugal flow coating method)

The suspension-G was treated in the same way as in EXAMPLE I-1 to prepare a catalyst. The ratio of elements other than oxygen in this catalyst oxide was $Co_3Ni_1Bi_1Fe_2Mo_{12}Si_{4.7}B_{2.0}K_{0.2}Al_{1.0}$.

EXAMPLES VIII-2-1 and VIII-2-2

(Tablet-forming method)

The suspension-G was treated according to EXAMPLE I-2 to prepare catalysts.

EXAMPLES VIII-3-1 and VIII-3-2

(Extrusion method)

The suspension-G was treated according to EXAMPLE I-3 to prepare catalysts.

[EXAMPLE IX]

Preparation of catalyst material suspension

In preparing a catalyst material suspension in the same way as in the preparation of the catalyst suspension for EXAMPLES I-1 to I-6 series, nickel nitrate was added together with cobalt nitrate, potassium nitrate was used in place of potassium hydroxide and arsenious acid was used in place of ammonium paratungstate. The resulting suspension is referred to as suspension-H.

EXAMPLE IX-1

(Centrifugal flow coating method)

The suspension-H was treated in the same way as in EXAMPLE I-1 to prepare a catalyst. The ratio of elements other than oxygen in this catalyst oxide was $Co_3Ni_1Bi_1Fe_2Mo_{12}Si_{4.7}As_{0.5}Tl_{0.05}$.

EXAMPLES IX-2-1 and IX-2-2

(Tablet-forming method)

The suspension-H was treated according to EXAMPLE I-2 to prepare catalysts.

EXAMPLES IX-3-1 and IX-3-2

(Extrusion method)

The suspension-H was treated according to EXAMPLE I-3 to prepare catalysts.

EXAMPLES IX-4-1 and IX-4-2

(Marmerizer-forming method)

The suspension-H was treated according to EXAMPLE I-4 to prepare catalysts.

EXAMPLES IX-5-1 and IX-5-2

(Rolling particle-forming method)

The suspension-H was treated according to EXAMPLE I-5 to prepare catalysts.

EXAMPLES IX-6-1 and IX-6-2

(Pill-forming method)

The suspension-H was treated according to EXAMPLE I-6 to prepare catalysts.

[EXAMPLE X]

The preparation of the suspension for EXAMPLES I-1 to I-6 series was repeated to prepare a suspension. This suspension is referred to as suspension I. The suspension-I was shaped, dried and fired in the same way as in EXAMPLE I-1 to prepare a catalyst. However, this EXAMPLE used 40% by weight aqueous solution of ammonium nitrate as a binder. Reaction test was carried out according to the method of EXAMPLES I-1 to I-6. The resulting catalyst had a specific surface area of 12.3 $m^2/g$, a pore volume of 0.51 cc/g and a pore volume distribution in which the pore volume consisting of pores having pore diameter in the range from 1 to 10 m was 55% and the pore volume consisting of pores having pore diameter in the range from 0.1 to less than 1 $\mu m$ pores was 45%. This catalyst exhibited performance that the conversion of propylene was 99.2 mol%, the yield of acrolein in a single flow was 85.7 mol% and that the yield of acrylic acid in a single flow was 9.1 mol%.

TABLE 1

| EXAMPLE | Forming method | Specific surface area ($m^2/g$) | Pore volume (cc/g) | Pore diameter distribution A[*1] | Pore diameter distribution B[*2] | Reaction temperature (°C.) | Conversion of propylene (mol %) | Yield in single flow (mol %) Acrolein | Yield in single flow (mol %) Acrylic acid |
|---|---|---|---|---|---|---|---|---|---|
| Example I-1 | Centrifugal flow coating method | 10.6 | 0.460 | 35 | 62 | 310 | 98.7 | 85.4 | 9.5 |
| Example I-2-1 | Tablet-forming method | 8.2 | 0.350 | 5 | 90 | 310 | 90.3 | 75.9 | 8.1 |
| Example I-2-2 | Tablet-forming method | 4.2 | 0.250 | 0 | 92 | 310 | 86.5 | 69.2 | 10.1 |
| Example I-3-1 | Extrusion method | 8.7 | 0.380 | 10 | 85 | 310 | 92.3 | 78.5 | 9.0 |
| Example I-3-2 | Extrusion method | 3.5 | 0.230 | 0 | 97 | 310 | 90.0 | 75.1 | 9.8 |
| Example I-4 | Marmerizer-forming method | 10.1 | 0.500 | 30 | 64 | 310 | 91.8 | 78.9 | 9.3 |
| Example I-5 | Rolling particle-forming method | 12.5 | 0.400 | 35 | 60 | 310 | 93.0 | 77.1 | 10.9 |

TABLE 1-continued

| EXAMPLE | Forming method | Specific surface area (m²/g) | Pore volume (cc/g) | Pore diameter distribution A[*1] | B[*2] | Reaction temperature (°C.) | Conversion of propylene (mol %) | Yield in single flow (mol %) Acrolein | Acrylic acid |
|---|---|---|---|---|---|---|---|---|---|
| Example I-6 | Pill-forming method | 9.5 | 0.380 | 35 | 59 | 310 | 93.4 | 77.6 | 10.0 |

[*1] Ratio (%) of pore volume consisting of pores having diameters in the range from 1 to 10 μm to the entire pore volume
[*2] Ratio (%) of pore volume consisting of pores having diameters in the range from 0.1 to 1 (exclusive) μm to the entire pore volume

TABLE 2

| EXAMPLE | Forming method | Batch No. | Specific surface area (m²/g) | Pore volume (cc/g) | Pore diameter distribution A[*1] | B[*2] | Reaction temperature (°C.) | Conversion of propylene (mol %) | Yield in single flow (mol %) Acrolein | Acrylic acid |
|---|---|---|---|---|---|---|---|---|---|---|
| Example II-1 | Centrifugal flow coating method | 1 | 10.5 | 0.460 | 33 | 65 | 310 | 98.9 | 85.5 | 9.7 |
| | " | 2 | 10.1 | 0.480 | 35 | 61 | 310 | 98.1 | 85.7 | 9.3 |
| | " | 3 | 10.3 | 0.450 | 33 | 64 | 310 | 98.5 | 85.2 | 9.4 |
| | " | 4 | 10.7 | 0.460 | 32 | 65 | 310 | 99.2 | 85.0 | 10.5 |
| Example II-2 | Tablet-forming method | 1 | 9.5 | 0.330 | 40 | 56 | 310 | 93.2 | 75.5 | 9.1 |
| | " | 2 | 4.0 | 0.250 | 15 | 75 | 310 | 88.7 | 73.7 | 8.4 |
| | " | 3 | 10.2 | 0.370 | 35 | 62 | 310 | 92.0 | 75.3 | 8.1 |
| | " | 4 | 7.4 | 0.350 | 43 | 53 | 310 | 90.6 | 76.0 | 9.1 |
| Example II-3 | Extrusion method | 1 | 7.5 | 0.350 | 35 | 60 | 310 | 91.9 | 78.7 | 9.5 |
| | " | 2 | 5.0 | 0.270 | 45 | 47 | 310 | 87.1 | 76.2 | 7.0 |
| | " | 3 | 8.1 | 0.360 | 37 | 62 | 310 | 92.1 | 79.1 | 8.9 |
| | " | 4 | 6.7 | 0.320 | 41 | 43 | 310 | 89.6 | 78.5 | 8.1 |
| Example II-4 | Rolling particle-forming method | 1 | 11.7 | 0.420 | 27 | 68 | 310 | 93.5 | 78.6 | 9.2 |
| | " | 2 | 10.1 | 0.450 | 18 | 72 | 310 | 90.5 | 77.9 | 8.5 |
| | " | 3 | 13.5 | 0.480 | 21 | 71 | 310 | 93.0 | 79.3 | 8.6 |
| | " | 4 | 8.6 | 0.360 | 35 | 57 | 310 | 89.1 | 77.4 | 8.6 |

[*1] & [*2] Same as the remarks to Table 1.

TABLE 3

| EXAMPLE | | Forming method | Specific surface area (m²/g) | Pore volume (cc/g) | Pore diameter distribution A[*1] | B[*2] | Reaction temperature (°C.) | Conversion of propylene (mol %) | Yield in single flow (mol %) Acrolein | Acrylic acid |
|---|---|---|---|---|---|---|---|---|---|---|
| III | III-1 | Centrifugal flow coating method | 12.5 | 0.410 | 32 | 60 | 310 | 99.5 | 87.8 | 7.2 |
| | III-2-1 | Tablet-forming method | 10.2 | 0.320 | 31 | 61 | 310 | 93.1 | 77.3 | 10.2 |
| | III-2-2 | Tablet-forming method | 7.8 | 0.230 | 45 | 46 | 310 | 87.9 | 74.2 | 9.3 |
| IV | IV-1 | Centrifugal flow coating method | 9.2 | 0.430 | 45 | 50 | 310 | 91.0 | 82.3 | 6.0 |
| | IV-2-1 | Extrusion method | 8.5 | 0.350 | 29 | 63 | 310 | 88.5 | 75.2 | 6.3 |
| | IV-2-2 | Extrusion method | 6.9 | 0.180 | 0 | 92 | 310 | 85.1 | 68.9 | 7.3 |
| V | V-1 | Centrifugal flow coating method | 10.5 | 0.430 | 35 | 59 | 310 | 98.3 | 88.9 | 6.1 |
| | V-2-1 | Marmerizer-forming method | 9.2 | 0.350 | 30 | 65 | 310 | 92.7 | 78.8 | 9.5 |
| | V-2-2 | Marmerizer-forming method | 8.7 | 0.270 | 32 | 61 | 310 | 90.3 | 77.1 | 8.9 |
| VI | VI-1 | Centrifugal flow coating method | 11.2 | 0.420 | 38 | 60 | 310 | 98.7 | 87.8 | 6.0 |
| | VI-2-1 | Rolling particle-forming method | 10.2 | 0.350 | 33 | 61 | 310 | 94.3 | 81.0 | 7.0 |
| | VI-2-2 | Rolling particle-forming method | 7.8 | 0.280 | 27 | 65 | 310 | 90.2 | 79.0 | 7.3 |
| VII | VII-1 | Centrifugal flow coating method | 10.7 | 0.380 | 34 | 58 | 310 | 95.6 | 81.0 | 9.6 |
| | VII-2-1 | Pill-forming method | 10.2 | 0.300 | 37 | 57 | 310 | 91.3 | 75.8 | 8.4 |
| | VII-2-2 | Pill-forming method | 7.9 | 0.260 | 41 | 50 | 310 | 88.5 | 73.5 | 8.7 |
| VIII | VIII-1 | Centrifugal flow coating method | 9.5 | 0.350 | 30 | 65 | 310 | 93.0 | 74.1 | 9.6 |
| | VIII-2-1 | Tablet-forming method | 9.0 | 0.310 | 10 | 82 | 310 | 89.3 | 71.4 | 8.3 |
| | VIII-2-2 | Tablet-forming method | 8.5 | 0.250 | 0 | 90 | 310 | 86.1 | 69.2 | 7.1 |
| IX | IX-1 | Centrifugal flow coating method | 10.3 | 0.420 | 34 | 60 | 310 | 97.2 | 81.6 | 6.3 |
| | IX-2-1 | Tablet-forming method | 9.7 | 0.320 | 30 | 59 | 310 | 90.1 | 75.7 | 6.1 |

TABLE 3-continued

| EXAMPLE | Forming method | Specific surface area (m²/g) | Pore volume (cc/g) | Pore diameter distribution A*1 | B*2 | Reaction temperature (°C.) | Conversion of propylene (mol %) | Yield in single flow (mol %) Acrolein | Acrylic acid |
| --- | --- | --- | --- | --- | --- | --- | --- | --- | --- |
| IX-2-2 | Tablet-forming method | 8.5 | 0.250 | 0 | 89 | 310 | 88.2 | 73.4 | 6.0 |
| IX-3-1 | Extrusion method | 9.0 | 0.370 | 27 | 68 | 310 | 93.1 | 76.1 | 7.1 |
| IX-3-2 | Extrusion method | 8.8 | 0.270 | 0 | 93 | 310 | 90.3 | 74.7 | 6.7 |
| IX-4-1 | Marmerizer-forming method | 9.2 | 0.360 | 35 | 60 | 310 | 93.2 | 76.9 | 7.1 |
| IX-4-2 | Marmerizer-forming method | 8.7 | 0.210 | 42 | 49 | 310 | 90.6 | 75.2 | 7.2 |
| IX-5-1 | Rolling particle-forming method | 11.2 | 0.420 | 41 | 55 | 310 | 94.1 | 77.6 | 7.5 |
| IX-5-2 | Rolling particle-forming method | 9.1 | 0.350 | 44 | 54 | 310 | 92.7 | 76.5 | 6.9 |
| IX-6-1 | Pill-forming method | 10.1 | 0.400 | 31 | 65 | 310 | 91.6 | 75.3 | 7.2 |
| IX-6-2 | Pill-forming method | 8.5 | 0.290 | 42 | 50 | 310 | 89.7 | 73.2 | 7.0 |

*1 & *2 Same as the remarks to Table 1.

[EXAMPLE XI]

Preparation of catalyst material suspension

Cobalt nitrate (14.56 kg) and 2.02 kg of ferric nitrate were dissolved in 10 liters of distilled water. 2.43 kg of bismuth nitrate was also dissolved in a nitric acid/distilled water solution consisting of 300 ml of concentrated nitric acid and 1,200 ml of distilled water. Separately, while 30 liters of distilled water was heated with stirring, 10.59 kg of ammonium paramolybdate and 2.65 kg of ammonium paratungstate were respectively added and dissolved therein, and the above two aqueous solutions of nitrate were added dropwise to the solution. And then an aqueous solution of 390 g of cesium nitrate in 1 liter of distilled water and 2.03 kg of 20%-by-weight-concentrated silica sol were consecutively added thereto and dissolved to obtain a suspension. (The resulting suspension is referred to as suspension-J.)

EXAMPLE XI-1-1

(Centrifugal flow coating method)

A part of the suspension-J was evaporated and dried to solidify it while it was heated with stirring, and then the resulting solid in the state of block was dried in a drier at 200° C. for 5 hours and milled to not more than 100 mesh to obtain a powder.

At first, alpha-alumina particles having the average diameter of 1 mm were charged into a centrifugal flow coating device. And then the above powder was charged into the device blowing heated air at 90° C. with using distilled water as a binder and formed into spherical particles having the average diameter of 5 mm. The resulting spherical particles were fired under an air current at 500° C. for 6 hours. The ratio of elements other than oxygen in this catalyst oxide was $Mo_{12}W_2Co_{10}Bi_1Fe_1Si_{1.35}Cs_{0.4}$.

EXAMPLE XI-1-2

(Centrifugal flow coating method)

EXAMPLE XI-1-1 was repeated except that 40% by weight aqueous solution of ammonium nitrate was used as a binder in place of distilled water, to prepare a catalyst.

EXAMPLES XI-2-1 and XI-2-2

(Tablet-forming method)

A part of the suspension-J was evaporated and dried with stirring under heat to produce a block state. The blocked product was dried in a drier under an air current at 200° C. for 5 hours. This dried block was milled to not more than 100 mesh. 2% by weight of a carbon powder was added to the milled powder and the resulting mixture was formed into tablets having a diameter of 5 mm and height of 5 mm. The tablets were fired under an air current at 500° C. for 6 hours to prepare a catalyst (XI-2-1). And then the same procedure was repeated to prepare a catalyst (XI-2-2).

EXAMPLES XI-3-1 and XI-3-2

(Extrusion method)

A part of the suspension-J was evaporated and condensed until it was extrudable, and extruded to form extrudates having a diameter of 5 mm and height of 5 mm. The extrudates were fired under air current at 500° C. for 6 hours to prepare a catalyst (XI-3-1). Then, the same procedure was repeated to prepare a catalyst (XI-3-2).

EXAMPLE XI-4

(Marmerizer-forming method)

A part of the suspension-J was treated with externally applied heat for condensation until it was extrudable. And the product was extruded to form extrudates having a diameter of 6 mm and lengths of 4 to 7 mm, and then the extrudates were subjected to a marmerizer to form elliptic spheres having a breadth of 3 mm and length of 5 mm. The elliptic spheres were fired under air current at 500° C. for 6 hours to prepare a catalyst (XI-4).

EXAMPLE XI-5

(Rolling particle-forming method)

A part of the suspension-J was evaporated and dried with stirring under heat to solidify it into a block state. The resulting solid was dried in a drier at 200° C. for 5 hours and milled to about 100 mesh to obtain a powder. At first, alpha-alumina having the average diameter of 1 mm was charged into a rolling particle-forming machine and then the above powder was charged into the machine. By the use of heated air at 80° C. and distilled water as a binder, the mixture was formed into spherical particles having the average diameter of 5 mm. The particles were fired under an air current at 500° C. for 6 hours to prepare a catalyst (XI-5).

EXAMPLE XI-6

(Pill-forming method)

A part of the suspension-J was treated with externally applied heat for condensation thereof to obtain a soil-like product, 50% by weight of which was dissipated when it was fired at 500° C. This product was formed into shapes having the average diameter of 5 mm by the use of a usual pill-forming machine. The resulting spherical product was fired under an air current at 500° C. for 6 hours to obtain a catalyst (XI-6).

REACTION TEST

Catalysts XI-1 to XI-6 obtained in the above EXAMPLES (1,500 ml each) were charged respectively to steel reaction tubes having an internal diameter of 25.4 mm, and a mixture gas composed of 6% by volume of isobutylene, 13.2% by volume of oxygen, 15% by volume of water vapor and 65.8% by volume of nitrogen was introduced thereinto to carry out reactions at reaction temperatures of 330° to 340° C. and at a space velocity of 1,600 hr$^{-1}$. The results are shown in Table 4.

XII-6) were prepared by the use of the suspension-J and six different forming methods shown in Table 5 according to EXAMPLE XI. In each of EXAMPLES XII-1 to XII-6, four catalysts were prepared under the same conditions (batch Nos. 1 to 4) in order to test the presence or absence of the reproducibility of catalyst preparation. Tests of performance were carried out according to the method of EXAMPLES XI-1 to XI-6 series. With regard to EXAMPLE XII-1, the method of EXAMPLE XI-1-1 was applied. The results are shown in Table 5.

As is clear in Table 5, it is seen that the formation by a centrifugal flow coating method can give catalysts having smaller variation of physical values and high activity. The fact that the variation of physical values is small means that catalysts were prepared with good reproducibility. On the other hand, it is further seen that catalysts prepared by the other forming methods include those that have not physical values specified by the present invention although they were prepared in batches under entirely the same conditions, and that the catalyst performance thereof is inferior to that of the catalysts obtained by a centrifugal flow coating method.

TABLE 4

| Example | Forming method | Specific surface area (m²/g) | Pore volume (cc/g) | Pore diameter distribution A*¹ | Pore diameter distribution B*² | Reaction temperature (°C.) | Conversion of isobutylene (mol %) | Selectivity Methacrolein | Selectivity Methacrolein acid | Total yield in single flow (mol %) |
|---|---|---|---|---|---|---|---|---|---|---|
| XI-1-1 | Centrifugal flow coating method | 30 | 0.420 | 58 | 39 | 330 | 99.3 | 85.1 | 3.4 | 87.9 |
| XI-1-2 | " | 2.9 | 0.415 | 56 | 40 | 330 | 99.5 | 86.0 | 3.0 | 88.6 |
| XI-2-1 | Tablet-forming method | 1.8 | 0.312 | 23 | 75 | 340 | 98.0 | 83.7 | 3.7 | 85.7 |
| XI-2-2 | " | 2.1 | 0.300 | 20 | 78 | 340 | 97.5 | 84.2 | 3.2 | 85.2 |
| XI-3-1 | Extrusion method | 2.2 | 0.350 | 35 | 63 | 340 | 98.6 | 84.0 | 3.5 | 86.3 |
| XI-3-2 | " | 2.0 | 0.372 | 31 | 66 | 340 | 98.1 | 84.4 | 3.0 | 85.7 |
| XI-4 | Marmerizer-forming method | 2.1 | 0.342 | 37 | 61 | 340 | 98.7 | 84.1 | 3.4 | 86.4 |
| XI-5 | Rolling particle-forming method | 2.7 | 0.372 | 42 | 55 | 340 | 98.2 | 84.7 | 2.2 | 85.3 |
| XI-6 | Pill-forming method | 2.6 | 0.321 | 35 | 63 | 340 | 97.8 | 84.1 | 2.7 | 84.9 |

*¹Ratio (%) of pore volume consisting of pores having diameters in the range from 1 to 10 μm to the entire pore volume
*²Ratio (%) of pore volume consisting of pores having diameters in the range from 0.1 to 1 (exclusive) μm to the entire pore volume

[EXAMPLE XII]

(Preparation of catalyst and its reproducibility)

A suspension-J was prepared in the same way as in EXAMPLE XI, and catalysts (EXAMPLES XII-1 to

TABLE 5

| Example | Forming method | Batch No. | Specific surface area (m²/g) | Pore volume (cc/g) | Pore diameter distribution A*¹ | Pore diameter distribution B*² | Reaction temperature (°C.) | Conversion of isobutylene (mol %) | Selectivity Methacrolein | Selectivity Methacrolein acid | Total yield in single flow (mol %) |
|---|---|---|---|---|---|---|---|---|---|---|---|
| XII-1 | Centrifugal flow coating method | 1 | 2.9 | 0.417 | 58 | 40 | 330 | 99.2 | 85.3 | 3.6 | 88.2 |
| | | 2 | 3.0 | 0.420 | 59 | 40 | 330 | 99.0 | 85.2 | 3.5 | 87.8 |
| | | 3 | 2.9 | 0.418 | 60 | 38 | 330 | 99.4 | 85.6 | 3.2 | 88.2 |
| | | 4 | 3.1 | 0.420 | 59 | 40 | 330 | 99.3 | 85.3 | 3.5 | 88.2 |
| XII-2 | Tablet-forming method | 1 | 1.7 | 0.312 | 20 | 77 | 340 | 98.1 | 83.6 | 3.5 | 85.4 |
| | | 2 | 1.5 | 0.297 | 19 | 80 | 340 | 97.6 | 83.1 | 3.5 | 84.5 |
| | | 3 | 1.1 | 0.253 | 24 | 75 | 340 | 97.2 | 83.7 | 3.6 | 84.9 |
| | | 4 | 2.0 | 0.330 | 18 | 80 | 340 | 98.2 | 82.2 | 3.2 | 85.8 |
| XII-3 | Extrusion method | 1 | 2.4 | 0.380 | 35 | 63 | 340 | 98.9 | 84.1 | 3.3 | 86.4 |
| | | 2 | 2.1 | 0.292 | 31 | 66 | 340 | 98.1 | 82.7 | 3.4 | 84.5 |
| | | 3 | 1.8 | 0.270 | 38 | 59 | 340 | 97.6 | 83.6 | 3.3 | 84.8 |
| | | 4 | 2.2 | 0.350 | 30 | 66 | 340 | 98.5 | 82.1 | 3.2 | 84.0 |
| XII-4 | Marmerizer-forming method | 1 | 2.5 | 0.301 | 35 | 64 | 340 | 98.1 | 82.7 | 3.4 | 84.5 |
| | | 2 | 2.0 | 0.295 | 28 | 71 | 340 | 97.2 | 82.5 | 3.4 | 83.5 |
| | | 3 | 2.2 | 0.300 | 30 | 68 | 340 | 97.8 | 83.5 | 3.2 | 84.8 |

TABLE 5-continued

| Example | Forming method | Batch No. | Specific surface area (m²/g) | Pore volume (cc/g) | Pore diameter distribution A*1 | Pore diameter distribution B*2 | Reaction temperature (°C.) | Conversion of isobutylene (mol %) | Selectivity Methacrolein | Selectivity Methacrolein acid | Total yield in single flow (mol %) |
|---|---|---|---|---|---|---|---|---|---|---|---|
| | | 4 | 2.6 | 0.312 | 37 | 61 | 340 | 98.3 | 82.1 | 3.4 | 84.0 |
| XII-5 | Rolling particle-forming method | 1 | 2.5 | 0.365 | 41 | 58 | 340 | 98.2 | 84.1 | 3.5 | 86.0 |
| | | 2 | 2.9 | 0.400 | 34 | 64 | 340 | 98.7 | 83.5 | 3.4 | 85.8 |
| | | 3 | 2.1 | 0.312 | 31 | 68 | 340 | 97.5 | 83.2 | 3.3 | 84.3 |
| | | 4 | 2.6 | 0.354 | 40 | 57 | 340 | 98.1 | 83.6 | 3.4 | 85.3 |
| XII-6 | Pill-forming method | 1 | 2.1 | 0.312 | 28 | 71 | 340 | 97.6 | 82.7 | 3.3 | 83.9 |
| | | 2 | 2.4 | 0.341 | 31 | 68 | 340 | 97.1 | 83.6 | 3.3 | 84.4 |
| | | 3 | 2.9 | 0.378 | 34 | 64 | 340 | 98.1 | 83.1 | 3.3 | 84.8 |
| | | 4 | 2.7 | 0.350 | 39 | 60 | 340 | 96.5 | 84.2 | 3.3 | 84.5 |

*1 & *2 Same as the remarks to Table 4

[EXAMPLE XIII]

Preparation of catalyst material suspension

EXAMPLE XI was repeated except that 230.9 g of rubidium nitrate and 50.5 g of potassium nitrate were used in place of cesium nitrate to obtain a suspension (the resulting suspension is referred to as suspension-K).

EXAMPLE XIII-1

(Centrifugal flow coating method)

A part of the suspension-K was treated in the same way as in EXAMPLE XI-1-1 to prepare a catalyst. The ratio of elements other than oxygen in this catalyst oxide was $Mo_{12}W_2Co_7Bi_3Fe_1Si_{1.35}Rb_{0.4}K_{0.1}$.

EXAMPLES XIII-2-1 and XIII-2-2

(Tablet-forming method)

A part of the suspension-K was treated in the same way as in EXAMPLE XI-2 to prepare a catalyst.

REACTION TEST

By the use of the catalysts obtained in EXAMPLES XIII-1 and XIII-2, reactions were carried out in the same way as in EXAMPLE XI. The results are shown in Table 6.

[EXAMPLE XIV]

Preparation of catalyst material suspension

EXAMPLE XIII was repeated except that 21.0 g of lithium hydroxide and 127.5 g of sodium nitrate were used in place of cesium nitrate and potassium nitrate to obtain a suspension (which is referred to as suspension-L).

EXAMPLE XIV-1

(Centrifugal flow coating method)

A part of the suspension-L was treated in the same way as in EXAMPLE XI-1-1 to prepare a catalyst. The ratio of elements other than oxygen in this catalyst oxide was $Mo_{12}W_2Co_7Bi_3Fe_1Si_{1.35}Li_{0.1}Na_{0.3}$.

EXAMPLES XIV-2-1 and XIV-2-2

(Extrusion method)

A part of the suspension-K was treated in the same way as in EXAMPLE XI-3 to prepare a catalyst.

REACTION TEST

By the use of the catalysts obtained in EXAMPLES XIV-1 and XIV-2, reactions were carried out in the same way as in EXAMPLE XI. The results are shown in Table 6.

[EXAMPLE XV]

Preparation of catalyst material suspension

EXAMPLE XI was repeated except that 115.3 g of 85% orthophosphoric acid was added after ammonium paratungstate and that 532.7 g of thallium nitrate was used in place of cesium nitrate, to obtain a suspension (which is referred to as suspension-M).

EXAMPLE XV-1

(Centrifugal flow coating method)

A part of the suspension-M was treated in the same way as in EXAMPLE XI-1-1 to prepare a catalyst. The ratio of elements other than oxygen in this catalyst oxide was $Mo_{12}W_2Co_{10}Bi_1Fe_1Si_{1.35}Tl_{0.4}P_{0.2}$.

EXAMPLES XV-2-1 and XV-2-2

(Marmerizer-forming method)

A part of the suspension-M was treated in the same way as in EXAMPLE XI-4 to prepare a catalyst.

REACTION TEST

By the use of the catalysts obtained in EXAMPLES XV-1 and XV-2, reactions were carried out in the same way as in EXAMPLE XI. The results are shown in Table 6.

[EXAMPLE XVI]

Preparation of catalyst material suspension

EXAMPLE XI was repeated except that 11.6 kg of nickel nitrate was used in place of cobalt nitrate and that 1.282 g of magnesium nitrate and 1,180.7 g of calcium nitrate were used together with 195 g of cesium nitrate, to obtain a suspension (which is referred to as suspension-N).

EXAMPLE XVI-1

(Centrifugal flow coating method)

A part of the suspension-N was treated in the same way as in EXAMPLE XI-1-1 to prepare a catalyst. The ratio of elements other than oxygen in this catalyst oxide was $Mo_{12}W_2Ni_8Bi_1Fe_1Si_{1.35}Cs_{0.2}Mg_{1.0}Ca_{1.0}$.

EXAMPLES XVI-2-1 and XVI-2-2

(Rolling particle-forming method)

A part of the suspension-N was treated in the ame way as in EXAMPLE XI-5 to prepare a catalyst.

REACTION TEST

By the use of the catalysts obtained in EXAMPLES XVI-1 and XVI-2, reactions were carried out in the same way as in EXAMPLE XI. The results are shown in Table 6.

[EXAMPLE XVII]

Preparation of catalyst material suspension

EXAMPLE XI was repeated except that 1,306.7 g of barium nitrate and 1,058.1 g of strontium nitrate were used in place of magnesium nitrate and calcium nitrate to obtain a suspension (which is referred to as suspension-O).

EXAMPLE XVII-1

(Centrifugal flow coating method)

A part of the suspension-O was treated in the same way as in EXAMPLE XI-1-1 to prepare a catalyst. The ratio of elements other than oxygen in this catalyst oxide was $Mo_{12}W_2Ni_8Bi_1Fe_1Si_{1.35}Cs_{0.2}Ba_{1.0}Sr_{1.0}$.

EXAMPLES XVII-2-1 and XVII-2-2

(Pill-forming method)

A part of the suspension-O was treated in the same way as in EXAMPLE XI-6 to prepare a catalyst.

REACTION TEST

By the use of the catalysts obtained in EXAMPLES XVII-1 and XVII-2, reactions were carried out in the same way as in EXAMPLE XI. The results are shown in Table 6.

[EXAMPLE XVIII]

Preparation of catalyst material suspension

In preparing a catalyst material suspension in the same way as in EXAMPLE XI, ammonium paratungstate was not used, the amount of ferric nitrate used was changed to 6.06 kg, the amount of cobalt ntirate used was changed to 10.2 kg, the amount of cesium nitrate used was changed to 97.5 g, the amount of 20%-by-weight-concentrated silica sol used was changed to 16.5 kg and 1,656 g of lead nitrate was added before the above silica sol, which gave a suspension. (The suspension is referred to as suspension-P).

EXAMPLE XVIII-1

(Centrifugal flow coating method)

A part of the suspension-P was treated in the same way as in EXAMPLE XI-1-1 to prepare a catalyst. The ratio of elements other than oxygen in this catalyst oxide was $Mo_{12}Co_7Bi_1Fe_3Si_{11}Cs_{0.1}Pb_{1.0}$.

EXAMPLES XVIII-2-1 and XVIII-2-2

(Tablet-forming method)

A part of the suspension-P was treated in the same way as in EXAMPLE XI-2 to prepare a catalyst.

REACTION TEST

By the use of the catalysts obtained in EXAMPLES XVIII-1 and XVIII-2, reactions were carried out in the same way as in EXAMPLE XI. The results are shown in Table 6.

[EXAMPLE XIX]

Preparation of catalyst material suspension

In preparing a catalyst material suspension in the same way as in EXAMPLE XI, ammonium paratungstate and cesium nitrate were not used, the amount of ferric nitrate used was changed to 6.06 kg, 8.7 kg of nickel nitrate and 399 g of titanium dioxide were used respectively in place of cobalt nirate and silica sol, 2.9 kg of antimony trioxide was added together with ammonium paramolybdate, and 753.4 g of stannic oxide and 399.0 g of tellulium dioxide were added before titanium dioxide, which gave a suspension. (The suspension is referred to as suspension-Q).

EXAMPLE XIX-1

(Centrifugal flow coating method)

A part of the suspension-Q was treated in the same way as in EXAMPLE XI-1-1 to prepare a catalyst. The ratio of elements other than oxygen in this catalyst oxide was $Mo_{12}Ni_6Bi_1Fe_3Ti_1Sb_{2.0}Sn_1Te_{0.5}$.

EXAMPLES XIX-2-1 and XIX-2-2

(Extrusion method)

A part of the suspension-P was treated in the same way as in EXAMPLE XI-3 to prepare a catalyst.

REACTION TEST

By the use of the catalysts obtained in EXAMPLES XIX-1 and XIX-2, reactions were carried out in the same way as in EXAMPLE XI. The results are shown in Table 6.

[EXAMPLE XX]

Preparation of catalyst material suspension

In preparing a catalyst material suspension in the same way as in EXAMPLE XI, ammonium paratungstate was not used, the amount of cobalt nitrate used was changed to 7.3 kg, the amount of ferric nitrate used was changed to 24.2 kg, 252.7 g of potassium nitrate was used in place of cesium nitrate and 1,875.6 g of aluminum nitrate was used in place of silica sol, which gave a suspension. (The suspension is referred to as suspension-R).

EXAMPLE XX-1

(Centrifugal flow coating method)

A part of the suspension-R was treated in the same way as in EXAMPLE XI-1-1 to prepare a catalyst. The ratio of elements other than oxygen in this catalyst oxide was $Mo_{12}Co_5Bi_1Fe_{12}Al_{1.0}K_{0.5}$.

EXAMPLES XX-2-1 and XX-2-2

(Marmerizer-forming method)

A part of the suspension-R was treated in the same way as in EXAMPLE XI-4 to prepare a catalyst.

REACTION TEST

By the use of the catalyst obtained in EXAMPLES XX-1 and XX-2, reactions were carried out in the same way as in EXAMPLE XI. The results are shown in Table 6.

[EXAMPLE XXI]

TABLE 6

| Example | | Forming method | Specific surface area (m²/g) | Pore volume (cc/g) | Pore diameter distribution A*¹ | Pore diameter distribution B*² | Reaction temperature (°C.) | Conversion of isobutylene (mol %) | Selectivity (mol %) Methacrolein | Selectivity (mol %) Methacrolein acid | Total yield in single flow (mol %) |
|---|---|---|---|---|---|---|---|---|---|---|---|
| XIII | XIII-1 | Centrifugal flow coating method | 3.5 | 0.453 | 59 | 38 | 330 | 98.8 | 85.7 | 4.0 | 88.6 |
| | XIII-2-1 | Tablet-forming | 2.1 | 0.334 | 28 | 71 | 340 | 95.1 | 83.1 | 4.4 | 83.2 |
| | XIII-2-2 | method | 2.6 | 0.342 | 23 | 76 | 340 | 97.7 | 82.6 | 4.3 | 84.8 |
| XIV | XIV-1 | Centrifugal flow coating method | 3.7 | 0.400 | 57 | 42 | 330 | 97.9 | 80.6 | 3.5 | 82.3 |
| | XIV-2-1 | Extrusion method | 2.7 | 0.351 | 36 | 62 | 340 | 97.1 | 78.0 | 4.5 | 80.1 |
| | XIV-2-2 | | 2.5 | 0.312 | 31 | 68 | 340 | 96.3 | 76.2 | 4.1 | 77.3 |
| XV | XV-1 | Centrifugal flow coating method | 2.6 | 0.376 | 53 | 45 | 330 | 95.0 | 86.0 | 2.2 | 83.8 |
| | XV-2-1 | Marmerizer-forming | 2.6 | 0.312 | 32 | 67 | 340 | 94.7 | 84.1 | 2.1 | 81.6 |
| | XV-2-2 | method | 2.5 | 0.307 | 30 | 69 | 340 | 94.0 | 84.0 | 1.9 | 80.7 |
| XVI | XVI-1 | Centrifugal flow coating method | 3.0 | 0.357 | 56 | 42 | 330 | 98.9 | 81.2 | 3.5 | 83.8 |
| | XVI-2-1 | Rolling particle- | 3.0 | 0.314 | 42 | 56 | 340 | 98.0 | 79.5 | 3.2 | 81.0 |
| | XVI-2-2 | forming method | 2.6 | 0.287 | 37 | 61 | 340 | 97.2 | 79.2 | 3.1 | 80.0 |
| XVII | XVII-1 | Centrifugal flow coating method | 3.4 | 0.326 | 62 | 37 | 330 | 98.1 | 79.3 | 3.5 | 80.5 |
| | XVII-2-1 | Pill-forming | 2.5 | 0.302 | 41 | 56 | 340 | 96.2 | 78.1 | 4.1 | 79.1 |
| | XVII-2-2 | method | 2.4 | 0.298 | 32 | 66 | 340 | 97.0 | 77.5 | 4.2 | 79.2 |
| XVIII | XVIII-1 | Centrifugal flow coating method | 3.2 | 0.321 | 63 | 35 | 330 | 93.5 | 78.9 | 3.0 | 76.6 |
| | XVIII-2-1 | Tablet-forming | 1.6 | 0.301 | 21 | 78 | 340 | 91.0 | 77.1 | 2.5 | 72.4 |
| | XVIII-2-2 | method | 1.4 | 0.278 | 28 | 71 | 340 | 89.2 | 78.2 | 2.4 | 71.9 |
| XIX | XIX-1 | Centrifugal flow coating method | 3.3 | 0.376 | 62 | 36 | 330 | 89.6 | 78.1 | 3.0 | 72.7 |
| | XIX-2-1 | Extrusion method | 2.6 | 0.342 | 41 | 57 | 340 | 89.1 | 76.0 | 2.5 | 69.9 |
| | XIX-2-2 | | 2.5 | 0.310 | 29 | 69 | 340 | 88.0 | 75.1 | 3.0 | 68.7 |
| XX | XX-1 | Centrifugal flow coating method | 2.9 | 0.362 | 57 | 42 | 330 | 94.8 | 76.0 | 4.0 | 75.8 |
| | XX-2-1 | Marmerizer-forming | 2.8 | 0.314 | 35 | 62 | 340 | 94.1 | 71.9 | 5.0 | 72.4 |
| | XX-2-2 | method | 2.4 | 0.276 | 27 | 70 | 340 | 93.6 | 70.3 | 5.5 | 70.9 |
| XXI | XXI-1 | Centrifugal flow coating method | 3.8 | 0.396 | 64 | 35 | 330 | 93.2 | 74.0 | 6.0 | 74.6 |
| | XXI-2-1 | Rolling particle- | 3.5 | 0.351 | 42 | 56 | 340 | 92.7 | 71.2 | 6.2 | 71.7 |
| | XXI-2-2 | forming method | 3.2 | 0.306 | 36 | 61 | 340 | 92.0 | 69.5 | 6.1 | 69.6 |

*¹ & *² Same as the remarks to Table 4

Preparation of catalyst material suspension

In preparing a catalyst material suspension in the same way as in EXAMPLE XI, ammonium paratungstate was not used, 1,336.3 g of zirconyl nitrate was used in place of silica sol, the amount of cobalt nitrate used was changed to 8.7 kg and 1,435.2 g of manganese nitrate, 1,487.4 g of zinc nitrate and 664.5 g of niobium pentaoxide were used at the last step, which gave a suspension. (The suspension is referred to as suspension-S.)

EXAMPLE XXI-1

(Centrifugal flow coating method)

A part of the suspension-S was treated in the same way as in EXAMPLE XI-1-1 to prepare a catalyst. The ratio of elements other than oxygen in this catalyst oxide was $Mo_{12}Co_6Bi_1Fe_1Zr_1Cs_{0.4}Ce_1Mn_1Zn_1Nb_{0.5}$.

EXAMPLES XXI-2-1 and XXI-2-2

(Rolling particle-forming method)

A part of the suspension-S was treated in the same way as in EXAMPLE XI-5 to prepare a catalyst.

REACTION TEST

By the use of the catalysts obtained in EXAMPLES XXI-1 and XXI-2, reactions were carried out in the same way as in EXAMPLE XI. The results are shown in Table 6.

[EXAMPLE XXII]

A reaction was carried out by the use of the catalyst obtained in batch No. 1 of EXAMPLE XII-1 and tertiary butanol in place of isobutylene. In the reaction test, EXAMPLE XII was repeated except that 6% by volume of tertiary butanol was used in place of isobutylene. (Accordingly, the gas after a dehydration reaction of tertiary butanol was composed, on an average, of 5.66% by volume of isobutylene, 12.45% by volume of oxygen, 19.81% by volume of water vapor and 62.08% by volume of nitrogen. And the space velocity was 1,700 hr⁻¹.) The results of the reaction were that the conversion ratio of tertiary butanol was 100 mole%, the selectivity to methacrolein was 84.9%, the selectivity to methacrylic acid was 3.4% and unreacted isobutylene was 1.3%. Based on this reaction, it is seen that the same result is obtained even if isobutylene is changed to tertiary butanol.

[EXAMPLE XXIII]

By the use of the catalyst obtained in batch No. 2 of EXAMPLE XII-1, the reaction test for a long period of time of 8,000 hours was carried out. Said reaction test was carried out in the same way as in EXAMPLE XII. The temperature at the beginning of the reaction was 330° C. and it was sufficient to raise the reaction temperature by only 10° C. during the period of 8,000 hours. The results of the reaction at the time after 8,000 hours were that the conversion of isobutylene was 98.7 mol%, the selectivity to methacrolein was 85.3 mol% and the selectivity to methacrylic acid was 3.2 mol%.

What is claimed is:

1. A catalyst useful for producing, by catalytic gas phase oxidation of a $C_3$-$C_5$ olefin or tertiary alcohol, the corresponding unsaturated aldehyde and unsaturated carboxylic acid, said catalyst being obtained by forming particles of an unfired material powder comprising molybdenum, iron and bismuth in a centrifugal flow coating device, and then firing the particles, said catalyst having a specific surface area in the range of rom 1 to 20 $m^2$/gr, a pore volume in the range of from 0.1 to 1.0 cc/gr and a pore diameter distribution in which the pore diameters are collectively distributed in the range of each of from 1 to 10 microns and from 0.1 to less than 1 micron.

2. A process for preparing a catalyst comprising molybdenum, iron and bismuth and useful for producing, by catalytic gas phase oxidation of a $C_3$-$C_5$ olefin or tertiary alcohol, the corresponding unsaturated aldehyde and unsaturated carboxylic acid, said process comprising charging an unfired material powder comprising molybdenum, iron and bismuth into a centrifugal flow coating device to form particles having an average diameter of 2 to 10 mm and then firing the particles thereby to obtain, with good reproducibility, said catalyst which has a specific surface area in the range from 1 to 20 $m^2$/gr, a pore volume in the range of from 0.1 to 1.0 cc/gr and a pore diameter distribution in which the pore diameters are collectively distributed in the range of each of from 1 to 10 microns and from 0.1 to less than 1 micron.

3. A catalyst useful for the oxidation of a $C_3$-$C_5$ olefin according to claim 1 having a specific surface area in the range of from 5 to 20 $m^2$/gr, a pore volume in the range of from 0.3 to 0.9 cc/gr and a pore diameter distribution in which the pore diameters are collectively distributed in the range of each of from 1 to 10 microns and from 0.1 to less than 1 micron.

4. A process for preparing a catalyst comprising molybdenum, iron and bismuth useful for the oxidation of said unfired material powder into a centrifugal flow coating device to form particles having an average diameter of 2 to 10 mm and then firing the particles thereby to obtain the catalyst which has a specific surface area in the range from 5 to 20 $m^2$/gr, a pore volume in the range from 0.3 to 0.9 cc/gr and a pore diameter distribution in which the pore diameters are collectively distributed in the range of each of from 1 to 10 microns and from 0.1 less than to 1 micron.

5. A catalyst useful for the oxidation of isobutylene or tertiary butanol according to claim 1 characterized by comprising molybdenum, iron and bismuth, and at least one nickel and cobalt, wherein said unfired material powder particles formed in said centrifugal flow coating device further comprises at least one of nickel and cobalt and having a specific surface area in the range from 1 to 20 $m^2$/gr, a pore volume in the range of from 0.1 to 1.0 cc/gr and a pore diameter distribution in which the pore diameters are collectively distributed in the range of each of from 1 to 10 microns and from 0.1 to less than 1 micron.

6. A process for preparing a catalyst comprising molybdenum, iron and bismuth useful for the oxidation of isobutylene or tertiary butanol according to claim 2 characterized by charging said unfired material powder into a centrifugal flow coating device to form particles having an average diameter of 2 to 10 mm and then firing the particles thereby to obtain said catalyst which has a specific surface area in the range of from 1 to 20 $m^2$/gr, a pore volume in the range from 0.1 to 1.0 cc/gr and a pore diameter distribution in which the pore diameters are collectively distributed in the range of each of from 1 to 10 microns and from 0.1 less than to 1 micron.

7. A catalyst according to claim 3 useful for the oxidation of propylene, said catalyst having a composition represented by the following formula:

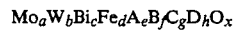
$$Mo_aW_bBi_cFe_dA_eB_fC_gD_hO_x$$

wherein Mo denotes molybdenum, W denotes tungsten, Bi denotes bismuth, Fe denotes iron, A denotes at least one element selected from the group consisting of nickel and cobalt, B denotes at least one element selected from the group consisting of alkali metal, alkaline earth metal and thallium, C denotes at least one element selected from the group consisting of phosphorus, tellurium, antimony, tin, cerium, lead, niobium, boron, arsenic, manganese and zinc, D denotes at least one element selected from the group consisting of silicon, aluminum, titanium and zirconium, and O denotes oxygen; and further a, b, c, d, e, f, g, h and x denote atomic ratios respectively, and when $a=2$ to 12, $b=0$ to 10 and $a+b=12$, then $c=0.1$ to 10, $d=0.1$ to 10.0, $e=2$ to 20, $f=0.005$ to 3.0, $g=0$ to 4.0, $h=0.5$ to 15 and x is a numerical value determined depending upon the atomic values of the other elements than oxygen and wherein said unfired material powder particles formed in said centrifugal flow coating device further comprise at least one of nickel and cobalt, at least one of alkali metal, alkaline earth metal and thallium, at least one of silicon, aluminum, titanium and zirconium, and optionally, at least one of phosphorus, tellurium, antimony, tin, cerium, lead, niobium, boron, arsenic, manganese, zinc and tungsten.

8. The catalyst of claim 7 in which the pore diameter distribution is such that the pore volume consisting of pores having pore diameters in the range of from 0.1 to less than 1 micron is not less than 30% based on the entire pore volume and the pore volume consisting of pores having pore diameters in the range of from 1 to 10 microns is not less than 20%, based on the entire pore volume.

9. The catalyst of claim 7 wherein the pore diameter distribution is such that the pore volume consisting of pores having pore diameters in the range of from 0.1 to less than 1 micron is in the range of from 45 to 80%, based on the entire pore volume, and the pore volume consisting of pores having pore diameters in the range of from 1 to 10 microns is in the range of from 25 to 60%, based on the entire pore volume.

10. The catalyst of claim 5 having a composition represented by the following formula:

$$Mo_aW_bBi_cFe_dA_eB_fC_gD_hO_x$$

wherein Mo denotes molybdenum, W denotes tungsten, Bi denotes bismuth, Fe denotes iron, A denotes at least one element selected from the group consisting of nickel and cobalt, B denotes at least one element selected from the group consisting of alkali metal, alkaline earth metal and thallium, C denotes at least one element selected from the group consisting of phosphorus, tellurium, antimony, tin, cerium, lead, niobium, boron, arsenic, manganese and zinc, D denotes at least one element selected from the group consisting of silicon, aluminum, titanium and zirconium, and O denotes oxygen; and further a, b, c, d, e, f, g, h and x denote atomic ratios respectively, and when $a=12$, then $b=0$ to 10, $c=0.1$ to 10, $d=0.1$ to 20, $e=2$ to 20, $f=0$ to 10, $g=0$ to 4, $h=0$ to 30 and x is a numerical value determined depending upon the atomic values of the other elements than oxygen, and wherein said unfired material powder particles formed in said centrifugal flow coating device further comprise at least one of nickel and cobalt, and optionally at least one of alkali metal, alkaline earth metal, thallium, phosphorus, tellurium, antimony, tin, cerium, lead, niobium, boron, arsenic, maganese, zinc, silicon, aluminum, titanium, zirconium and tungsten.

11. The catalyst of claim 10 wherein the pore diameter distribution is such that the ratio of the pore volume consisting of pores having pore diameters in the range of from 1 to 10 microns is greater than the ratio of the pore volume consisting of pores having pore diameters in the range of from 0.1 to less than 1 micron.

12. The process for preparing a catalyst comprising molybdenum, iron and bismuth according to claim 2 which comprises charging said unfired material powder into said centrifugal flow coating device, blowing heated air onto said powder, and spraying a binder onto said heated powder and recovering said formed particles having an average diameter of 2 to 10 mm and thereafter firing said particles.

13. The process of claim 12 wherein said binder is water and wherein said recovered particles are dried before firing.

14. The process of claim 2 which comprises charging said unfired material powder together with a binder selected from the group consisting of water, cellulose, ammonium nitrate, graphite, starch and organic solvents.

15. The catalyst according to claim 1 which is diluted with or supported on an inert carrier.

* * * * *

UNITED STATES PATENT AND TRADEMARK OFFICE
CERTIFICATE OF CORRECTION

PATENT NO. : 4,873,217
DATED : October 10, 1989
INVENTOR(S) : Tatsuya Kawajiri, Hideo Onodera, Shinichi Uchida, Yukio Aoki and Masahiro Wada It is certified that error appears in the above-identified patent and that said Letters Patent is hereby corrected as shown below:

Claim 1, line 8, delete "rom", insert --from--.

Claim 4, before line 3, insert --propylene according to claim 2 characterized by charging--

Claim 4, line 11, before "less", insert --to-- and after "than" delete "to".

Claim 6, line 12, after "0.1", insert --to--; and after "than", delete "to".

Signed and Sealed this

Fourth Day of September, 1990

Attest:

HARRY F. MANBECK, JR.

Attesting Officer

Commissioner of Patents and Trademarks